US012807547B2

(12) United States Patent
Senetar et al.

(10) Patent No.: US 12,807,547 B2
(45) Date of Patent: Nov. 24, 2026

(54) SYSTEMS AND METHODS FOR PARAFFIN CRACKING

(71) Applicant: UOP LLC, Des Plaines, IL (US)

(72) Inventors: John J. Senetar, Naperville, IL (US); Manuela Serban, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 266 days.

(21) Appl. No.: 18/394,291

(22) Filed: Dec. 22, 2023

(65) Prior Publication Data

US 2024/0217898 A1 Jul. 4, 2024

Related U.S. Application Data

(60) Provisional application No. 63/436,069, filed on Dec. 29, 2022.

(51) Int. Cl.

*C07C 4/06* (2006.01)
*B01J 21/12* (2006.01)
*C07C 5/03* (2006.01)

(52) U.S. Cl.

CPC ................. *C07C 4/06* (2013.01); *B01J 21/12* (2013.01); *C07C 5/03* (2013.01); *C07C 2521/12* (2013.01)

(58) Field of Classification Search

CPC ......... C07C 4/06; C07C 5/03; C07C 2521/12; B01J 21/12; C10G 51/026; C10G 69/04
USPC ........................................................... 585/251
See application file for complete search history.

(56) References Cited

U.S. PATENT DOCUMENTS

| | | | |
|---|---|---|---|
| 6,388,161 B1 | 5/2002 | Dath et al. | |
| 6,646,176 B1 | 11/2003 | Dath et al. | |
| 8,609,567 B2 | 12/2013 | Voskoboynikov et al. | |
| 11,078,435 B2 | 8/2021 | Senetar et al. | |
| 2005/0234282 A1 | 10/2005 | Bach et al. | |
| 2009/0143629 A1 * | 6/2009 | Voskoboynikov | C07C 11/06 585/314 |

FOREIGN PATENT DOCUMENTS

| | | |
|---|---|---|
| WO | 2011057975 A2 | 5/2011 |
| WO | 2012021345 A2 | 2/2012 |
| WO | 2012087440 A1 | 6/2012 |
| WO | 2013098199 A1 | 7/2013 |
| WO | 2016098909 A1 | 6/2016 |

OTHER PUBLICATIONS

International Search Report from corresponding PCT application No. PCT/US2023/086188, mailed May 2, 2024.
Written Opinion from corresponding PCT application No. PCT/US2023/086188, mailed May 2, 2024.
Extended European Search Report from corresponding European application No. 23913714.4, dated Oct. 14, 2026.

* cited by examiner

*Primary Examiner* — Prem C Singh
*Assistant Examiner* — Francis C Campanell

(57) ABSTRACT

Processes for cracking petroleum products such as paraffin and olefins to generate light olefins and having increased olefin production are described. A paraffin-rich feed stream is cracked in an olefin cracking reactor. Light olefins are removed from the olefin cracking effluent stream. A $C_4$-$C_5$ stream from the olefin cracking reactor effluent is cracked in a paraffin cracking reactor, and the paraffin cracking reactor effluent is sent to the olefin cracking reactor.

20 Claims, 4 Drawing Sheets

SYSTEMS AND METHODS FOR PARAFFIN CRACKING

RELATED APPLICATIONS

This application claims priority to U.S. Provisional Patent Application Ser. No. 63/436,069, filed on Dec. 29, 2022, the entirety of which is incorporated herein by reference.

BACKGROUND

Light olefins serve as feed materials for the production of numerous chemicals. Light olefins, primarily ethylene and propylene, serve as feeds for the production of plastics and petrochemicals. Conventionally, light olefins are produced by steam cracking or catalytic cracking. However, limitations associated with the conventional processes for making light olefins result in the demand for light olefins exceeding the supply.

The integration of olefin cracking processes (OCPs) into refining and petrochemical complexes has lead to increased paraffin content of feed streams. The olefin content of these feed streams is relatively low, and the recycle streams consequently have even lower olefin content.

There is a need for improved processes for the production of light olefins.

Figure 1:
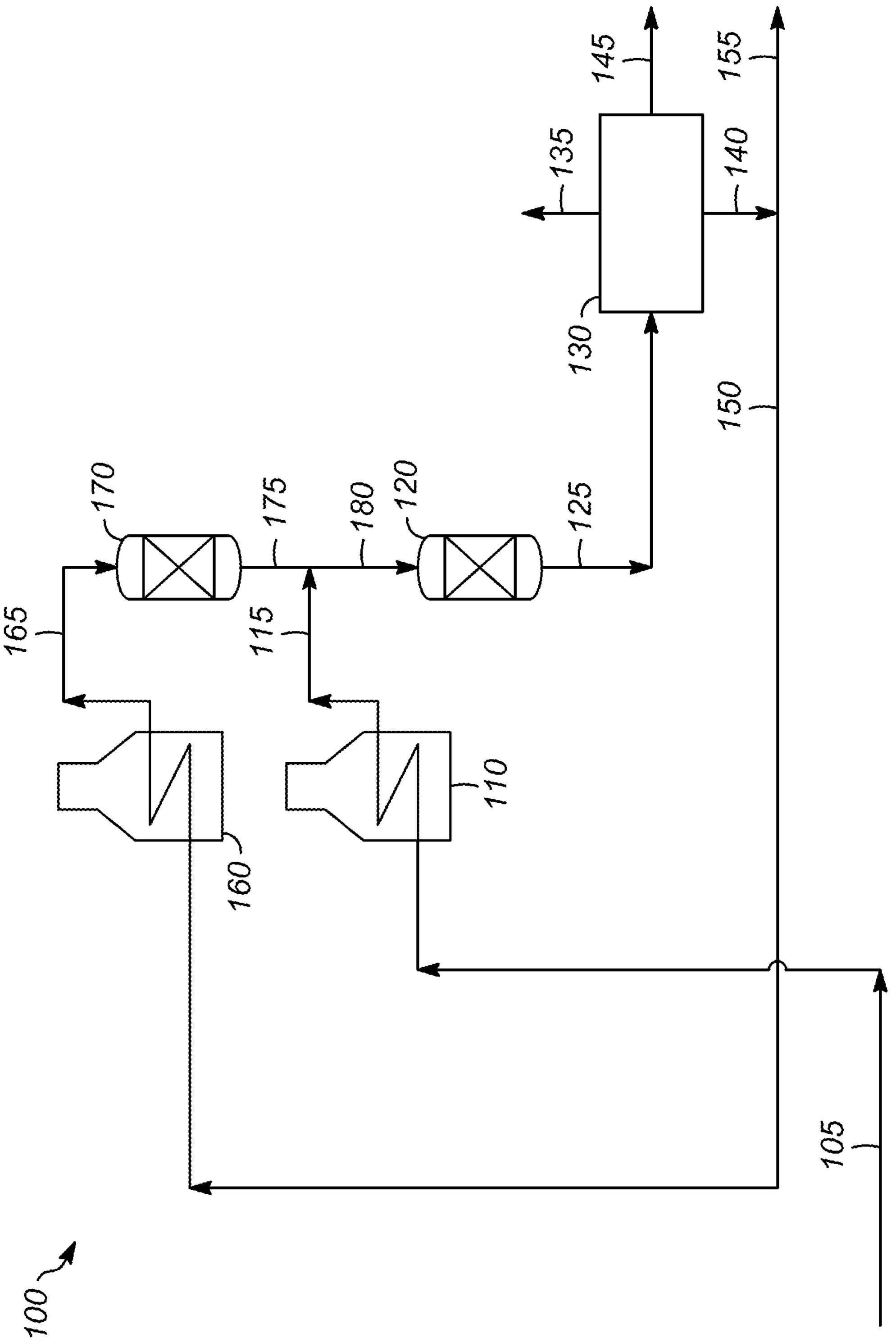
FIG. 1 schematically illustrates an exemplary process as provided herein.

The drawings set forth herein are illustrative of exemplary embodiments provided herein and are not meant to limit the scope of the invention as encompassed by the claims.

Like reference symbols in the various drawings indicate like elements.

DESCRIPTION

The present invention relates to processes for the production of light olefins, such as ethylene and propylene. The processes use staged OCP reactors to increase light olefin yield by cracking a paraffin-rich recycle stream in the first stage, and then sending the first stage effluent along with fresh paraffin-rich feed to a second stage. The paraffin cracking in the first stage should be greater due to the low olefin content of the recycle. The first stage effluent and the fresh feed will then be preferentially cracked in the second stage. The processes improve the conversion of the olefinic feed to lower hydrocarbons with improved weight hourly space velocity (WHSV) to reduce over-cracking of the feed and subsequent generation of excessive heavies. The processes also provide cost benefits in terms of lower capital and operational expenditures.

The olefin cracking processes (OCPs) crack paraffin and olefins to generate light olefins such as ethylene and propylene. The olefinic feed comprises diolefins and monoolefins. The recycle stream recovered from the separation process following the olefin cracking reactor is depleted in light olefins. This olefin-depleted stream has a higher paraffin content than the fresh feed (for example, the paraffin-comprising feedstock or the olefin-comprising feed or the combination thereof) and the combined feed. This depleted olefin steam lends itself to cracking at more severe conditions to convert the paraffins to olefins, thereby increasing the overall olefin yield from the process.

The feed stream comprises a mixture of $C_{4+}$ olefins and greater than or equal to 30 wt % paraffins. The feed stream may comprise cracked petroleum products derived from a petroleum source such as a heavy petroleum feedstock, for example, a feedstock comprising a vacuum gas oil or a reduced crude oil.

The process may optionally include selectively hydrogenating olefin-containing streams to saturate diolefins and acetylenes. Selective hydrogenation will result in about 50% to 99% of the diolefins and acetylenes being converted to olefins. This saturation step can be applied to a fresh feed stream or to a recycle stream within the OCP process, or a combined fresh feed and recycle stream may be treated in a single selective hydrogenation step. Typical selective hydrogenation conditions include a temperature of between about 40° C. and 140° C. and a pressure in a range of about 1.4 MPa(a) to 4.1 MPa(a). In some embodiments, the hydrogenation catalyst may comprise nickel, palladium, platinum, silver, tungsten disulphide, colloidal molybedunum on active carbon or molybdenum trioxide, or combinations thereof.

The paraffin-rich feed stream can be heated before entering the olefin cracking reactor, and/or the paraffin-rich recycle stream can be heated before entering the paraffin-rich reactor, and/or the paraffin cracking reactor effluent stream can be heated before entering the olefin cracking reactor. The temperature of one or more of these streams can be raised to the desired inlet temperature for the reactor involved. Any suitable heater can be used. Suitable heaters include, but are not limited to, heat exchangers, fired heaters, electric heaters, or combinations thereof, for example.

In some embodiments, the paraffin-rich feed stream and the paraffin-rich recycle stream can be heated with separate fired or electric charge heaters. Alternatively, a single fired or electric charge heater with separate tube passes can be used to heat the paraffin-rich feed stream and the paraffin-rich recycle stream.

In some embodiments, the paraffin-rich feed stream and/or the paraffin-rich recycle stream can be heat exchanged with the olefin reactor effluent stream. In some embodiments, the heat exchangers can be used in combination with fired or electric heaters.

In some embodiments, the paraffin cracking reactor effluent stream can be combined with the paraffin-rich feed stream, and the combined stream can be heated in a heater and/or heat exchanger before being sent to the olefin cracking reactor.

The paraffin cracking reactor effluent stream and the paraffin-rich feed stream are sent to the olefin cracking reactor, either separately or as a combined stream. When the streams are sent separately, they can be introduced at different locations in the olefin cracking reactor.

The paraffin-rich feed stream and the paraffin-rich recycle stream are sent to the olefin cracking reactor. The olefin cracking reactor inlet temperature is typically in the range of about 560° C. to about 620° C., or about 570° C. to about 590° C. The $C_{4+}$ olefins are cracked to form light olefins (i.e., ethylene and propylene). The reaction is endothermic, and the reactor outlet temperature is typically in the range of about 490° C. to about 550° C., or about 520° C. to about 540° C. The pressure at the outlet of the olefin cracking reactor is typically in the range of about 20 kPa(g) to 140 kPa(g).

The olefin reactor effluent stream comprises $C_4$ to $C_{10}$ olefins and 10 wt % or more of $C_4$ to $C_8$ paraffins.

The olefin cracking reactor effluent stream can be separated into a one or more streams. In some embodiments, it is separated into an olefin product stream comprising ethylene and propylene and any hydrogen, and a $C_4$-$C_5$ stream comprising butanes and pentanes. The $C_4$-$C_5$ stream will also include some $C_4$-$C_5$ olefins. In some embodiments, there can also be a heavy stream comprising $C_{6+}$ hydrocarbons and aromatics. Other separations could be utilized, as is known to those of skill in the art.

In some embodiments, the olefin reactor effluent stream is compressed before being separated. The olefin reactor effluent stream may be compressed to a pressure in the range of about 1.4 MPa(a) to about 2.8 MPa(a).

The $C_4$-$C_5$ stream may be divided into two portions, the paraffin-rich recycle stream and a purge stream. In some embodiments, the purge stream is removed to control the olefin content in the combined feed (the paraffin-rich feed stream and the paraffin-rich recycle stream). In some embodiments, the paraffin-rich recycle stream is adjusted to achieve 40-60 wt % olefin in the combined feed to the reactor. In some embodiments, about 30 wt % to about 80 wt % of the $C_{4-5}$ paraffins in the olefin reactor effluent are in the paraffin-rich recycle stream and about 20 wt % to about 70 wt % are in the purge stream.

The paraffin-rich recycle stream, which is depleted of olefins, may be heated as discussed above and sent to the paraffin cracking reactor where the paraffins are cracked. This arrangement provides enhanced paraffin cracking due to the absence (or reduced amount) of olefins in the paraffin cracking reactor.

The paraffin cracking reactor typically operates at a temperature in the range of operates about 490° C. to about 620° C. and a pressure in the range of about 135 kPa(a) to about 1050 kPa(a).

The paraffin cracking reactor effluent comprises ethylene and propylene converted from paraffins in the paraffin-rich recycle stream, $C_4$-$C_{10}$ olefins, and a reduced level of paraffins compared to the paraffin-rich recycle stream entering the paraffin cracking reactor.

The paraffin cracking reactor effluent is sent to the olefin cracking reactor which maximizes the conversion of the olefins to light olefins. About 10 wt % to about 60 wt % of the olefins are converted to light olefins in the olefin cracking reactor.

The catalysts in the olefin cracking reactor and the paraffin cracking reactor can be the same, or they can be different.

Any suitable olefin cracking catalyst can be used. Suitable olefin cracking catalysts include, but are not limited to, zeolites, aluminum oxide and silicon oxide, a faujasite, or combinations thereof. In some embodiments, the olefin cracking catalyst comprises a zeolite comprising silicalite having a silica to alumina ratio greater than 200, that is steam treated, acid washed, and loaded with an alkaline earth metal from the group consisting of magnesium (Mg), calcium (Ca), strontium (Sr), barium (Ba), or mixtures thereof. In some embodiments, the alkaline earth metal loading is in the range of about 0.1 weight (wt) % and 2 wt % of the catalyst. The catalyst may optionally further comprise a binder. In some embodiments, the binder comprises about 10 wt % and 75 wt % of the total catalyst weight. In some embodiments, catalyst is calcined.

In some embodiments, the catalyst in the olefin cracking reactor or the paraffin cracking reactor or both comprises a silicalite having a silica to alumina ratio greater than 200, and wherein the silicalite is steam treated, acid washed, and loaded with an alkaline earth metal.

In some embodiments, the catalyst in the olefin cracking reactor comprises a catalyst comprising a silicalite having a silica to alumina ratio greater than or equal to 200, and wherein the catalyst in the paraffin cracking reactor comprises an acidic catalyst.

Any suitable paraffin cracking catalyst can be used. Suitable paraffin cracking catalysts may comprise any of the olefin cracking catalysts described above. In addition, suitable paraffin cracking catalysts include acidic catalysts. Suitable acidic catalysts include, but are not limited to, zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. The 3-letter codes indicating a zeotype are as defined by the Structure Commission of the International Zeolite Association and are maintained at http://www.iza-structure.org/databases.

In some embodiments, the paraffin cracking catalyst comprises a silicalite having a silica to alumina ratio less than 200.

The paraffin cracking reactor and the olefin cracking reactor can be located in separate vessels. Alternatively, they can be located as separate beds in a single vessel.

FIG. 1 illustrates one embodiment of the process 100 for producing light olefins. The paraffin-rich feed stream 105 is heated in a first charge heater 110. The heated paraffin-rich feed stream 115 is sent to the olefin cracking reactor 120 where olefins in the paraffin-rich feed stream 105 are cracked to light olefins.

The olefin cracking reactor effluent stream 125 is passed to a separation zone 130. The olefin cracking reactor effluent stream 125 may optionally be compressed before being separated. The separation zone 130 comprises one or more fractionation columns where the olefin cracking reactor effluent stream 125 is separated into a olefin product stream 135 comprising ethylene and propylene, a $C_4$-$C_5$ stream 140 comprising butanes and pentanes, and a heavy stream 145 comprising $C_{6+}$ hydrocarbons.

The olefin product stream 135 is recovered, and the heavy stream 145 can be purged.

The $C_4$-$C_5$ stream 140 is divided into a paraffin-rich recycle stream 150 and a purge stream 155.

The paraffin-rich recycle stream 150 is sent to a second charge heater 160 where it is heated. The heated paraffin-rich recycle stream 165 is sent to the paraffin cracking reactor 170 where the paraffins are cracked to olefins.

The paraffin cracking reactor effluent stream 175 is combined with the heated paraffin-rich feed stream 115 forming combined stream 180. The combined stream 180 is sent to the olefin cracking reactor 120.

Alternatively, the first and second charge heaters 110, 160 could be replaced by a single charge heater with separate tube passes (not shown).

Figure 2:
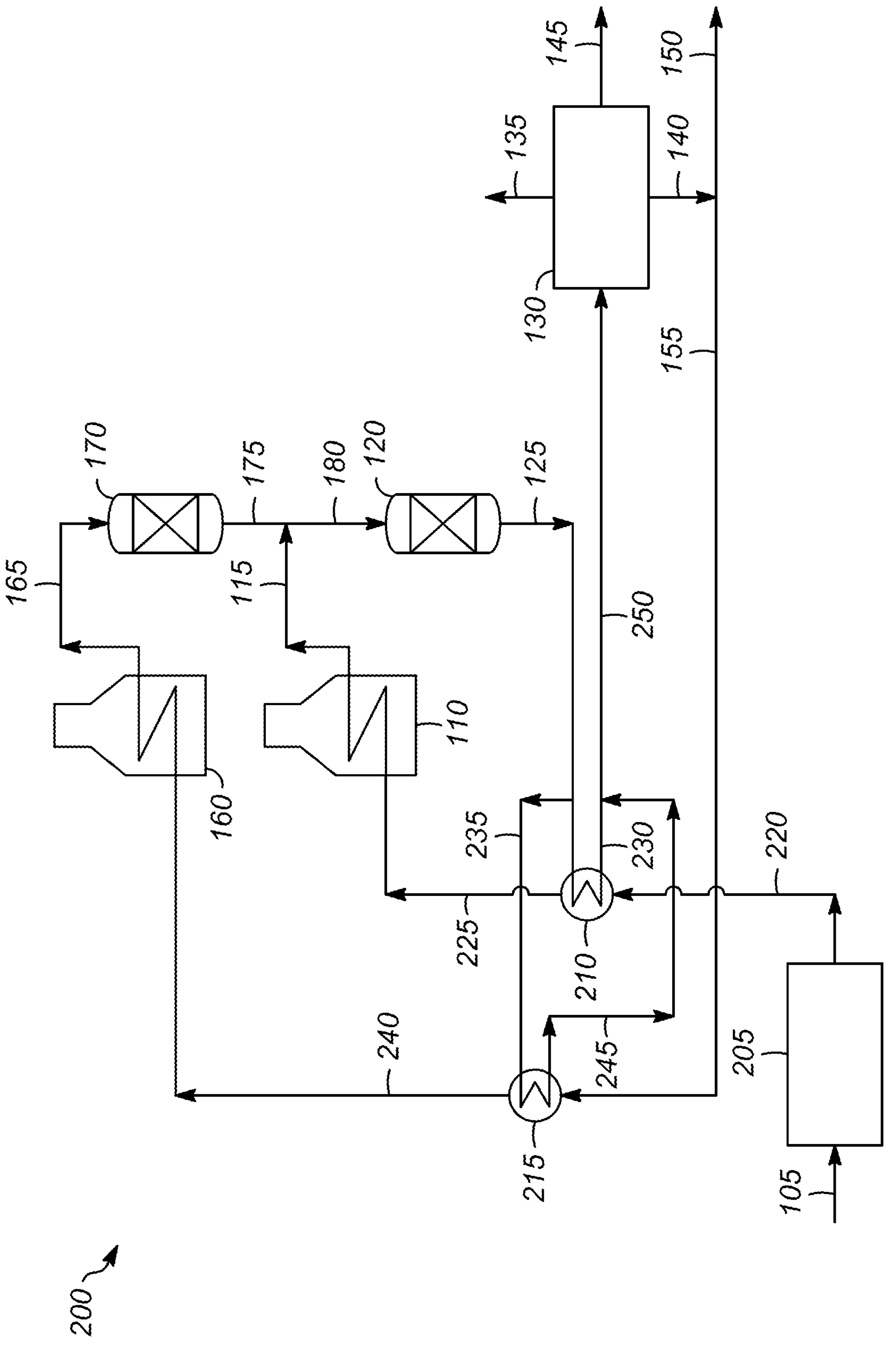
FIG. 2 schematically illustrates an exemplary process as provided herein.

FIG. 2 illustrates an alternate embodiment of the olefin cracking process 200. In this embodiment, a selective hydrogenation reactor 205 and first and second heat exchangers 210 and 215 are added.

The paraffin-rich feed stream 105 is selectively hydrogenated in selective hydrogenation reactor 205. The hydrogenated feed stream 220 is heated in the first heat exchanger 210 by heat exchange with the olefin cracking reactor effluent stream 125 forming partially heated hydrogenated feed stream 225 and first partially cooled olefin cracking reactor effluent stream 230.

The partially heated hydrogenated feed stream 225 is sent to the first charge heater 110 forming the heated paraffin-rich feed stream 115. The heated paraffin-rich feed stream 115 is sent to the olefin cracking reactor 120 where olefins in the paraffin-rich feed stream 105 are cracked to light olefins.

A portion 235 of the olefin cracking reactor effluent stream 125 is sent to the second heat exchanger 215 where it exchanges heat with the paraffin-rich recycle stream 150 forming a partially heated paraffin-rich recycle stream 240 and a second partially cooled olefin reactor effluent stream 245.

The first partially cooled olefin reactor effluent stream 230 and the second partially cooled olefin reactor effluent stream 245 are combined into the combined cooled olefin reactor effluent stream 250.

The combined cooled olefin reactor effluent stream 250 is passed to a separation zone 130. The olefin cracking reactor effluent stream 125 may optionally be compressed before being separated. The separation zone 130 comprises one or more fractionation columns where the olefin cracking reactor effluent stream 125 is separated into a olefin product stream 135 comprising ethylene and propylene, a $C_4$-$C_5$ stream 140 comprising butanes and pentanes, and a heavy stream 145 comprising $C_{6+}$ hydrocarbons.

The olefin product stream 135 is recovered, and the heavy stream 145 can be purged.

The $C_4$-$C_5$ stream 140 is divided into a paraffin-rich recycle stream 150 and a purge stream 155.

The partially heated paraffin-rich recycle stream 240 is sent to a second charge heater 160 where it is heated. The heated paraffin-rich recycle stream 165 is sent to the paraffin cracking reactor 170 where the paraffins are cracked to olefins.

The paraffin cracking reactor effluent stream 175 is combined with the heated paraffin-rich feed stream 115 forming combined stream 180. The combined stream 180 is sent to the olefin cracking reactor 120.

Alternatively, the first and second charge heaters 110, 160 could be replaced by a single charge heater with separate tube passes (not shown).

Figure 3:
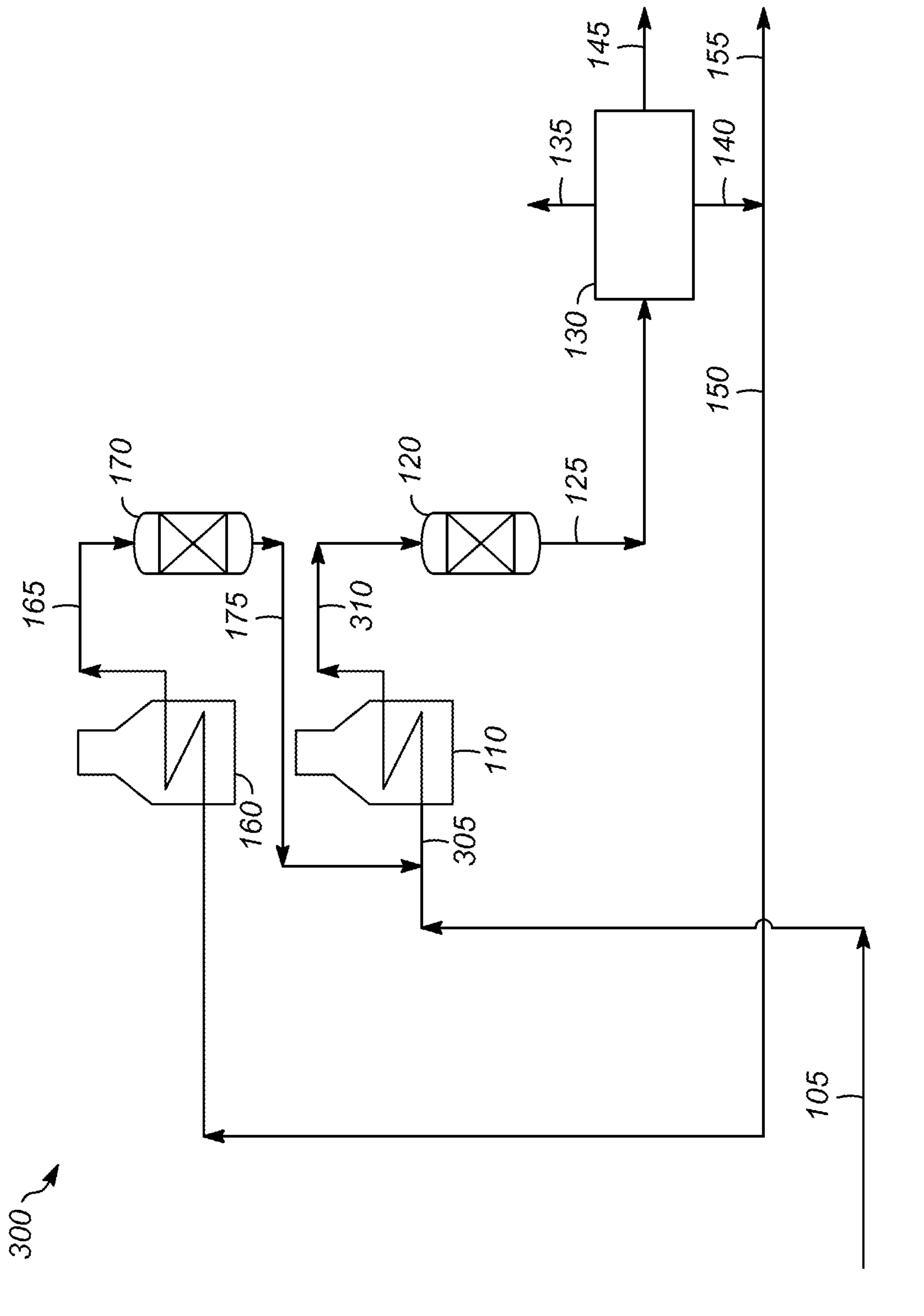
FIG. 3 schematically illustrates an exemplary process as provided herein.

FIG. 3 illustrates one embodiment of the process 300 for producing light olefins. The process 300 is similar to the process 100 of FIG. 1. In this process, instead of the paraffin cracking reactor effluent stream 175 being sent directly to the olefin cracking reactor 120, it is combined with the paraffin-rich feed stream 105 forming a combined stream 305. The combined stream 305 is sent to the first charge heater 110, and the heated combined stream 310 is sent to the olefin cracking reactor 120. This provides additional heating for the paraffin cracking reactor effluent stream 175. The additional heating increases conversion in the olefin cracking reactor 120 by achieving a high inlet temperature for the paraffin cracking reactor effluent stream 175 to the olefin cracking reactor 120. Alternatively, the temperature of the paraffin cracking reactor effluent stream 175 could be increased in a third charge reactor (not shown).

Figure 4:
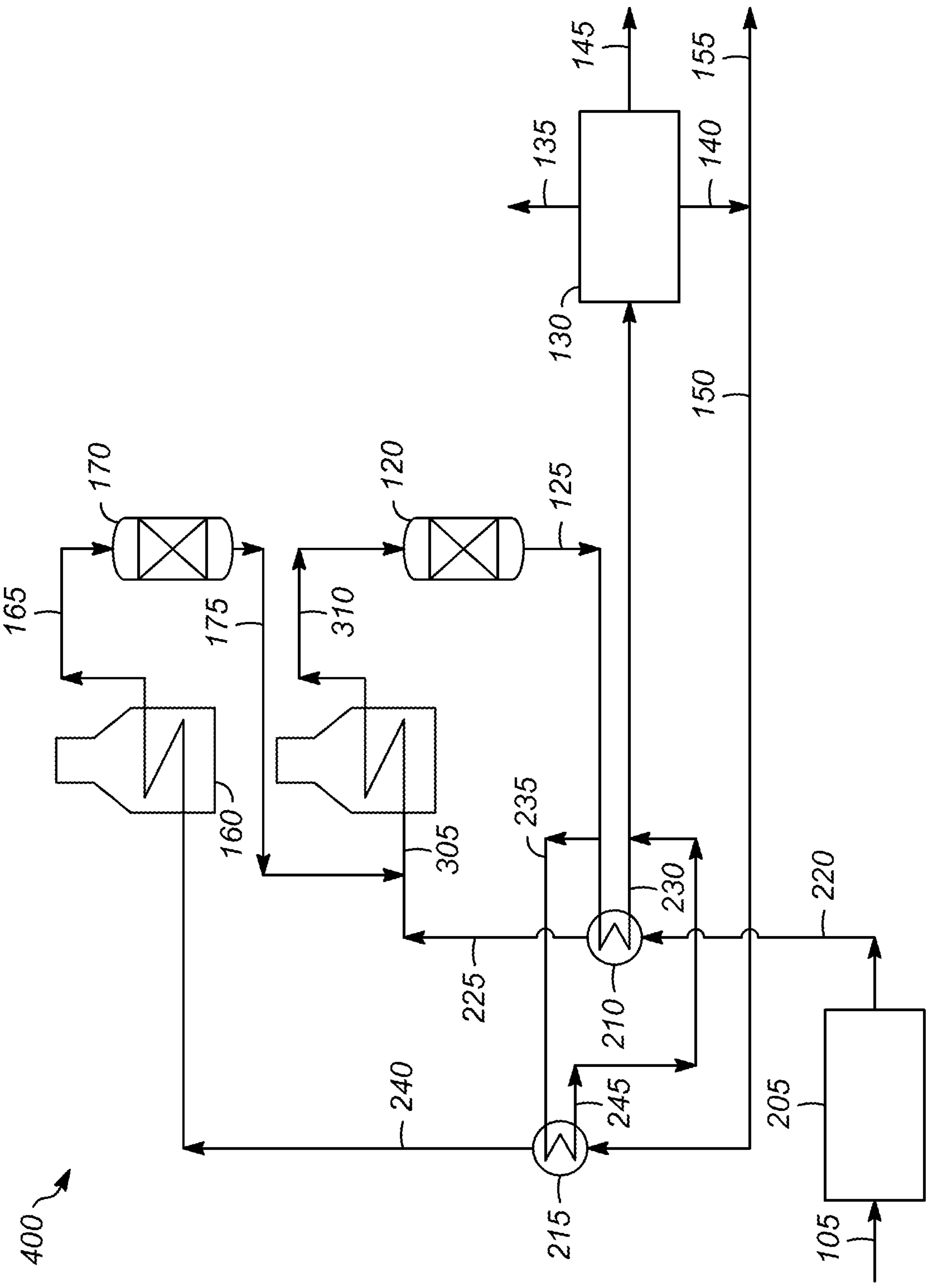
FIG. 4 schematically illustrates an exemplary process as provided herein.

FIG. 4 illustrates one embodiment of the process 400 for producing light olefins. The process 400 is similar to the process 200 of FIG. 2. In this process, instead of the paraffin cracking reactor effluent stream 175 being sent directly to the olefin cracking reactor 120, it is combined with the partially heated hydrogenated feed stream 225 forming a combined stream 305. The combined stream 305 is sent to the first charge heater 110, and the heated combined stream 310 is sent to the olefin cracking reactor 120. This increases conversion in the olefin cracking reactor 120 by achieving a high inlet temperature for the paraffin cracking reactor effluent stream 175 to the olefin cracking reactor 120. Alternatively, the temperature of the paraffin cracking reactor effluent stream 175 could be increased in a third charge reactor (not shown).

The invention will be further described with reference to the examples described herein; however, it is to be understood that the invention is not limited to such examples.

EXAMPLES

Example 1

In Example 1, a blend of 60 wt % iso-butane (i-C4) and 40 wt % iso-butene (iC4=) was subjected to catalytic cracking in the presence of a silicalite catalyst. The catalyst comprised a crystalline silicalite zeolite, with the silicalite having a silica to alumina ratio greater than 400, treated by steam and acid-washed, followed by drying and calcination. The feedstock was passed over the catalyst at a temperature of 580° C., a weight hourly space velocity (WHSV) of 6 $h^{-1}$, and total hydrocarbon pressure of 10 psig. The conversions, expressed as conversion of olefins and conversion of paraffins averaged over a period of time at which the test reached steady-state, are given in Table 1. In addition, Table 1 includes ethylene and propylene (wt %) amounts in the reaction effluent.

Conversion of Olefins=100*(Olefins in the Feed−Olefins in Effluent)/Olefins in Feed Conversion of Paraffins=100*(Paraffins in the Feed−Paraffins in Effluent)/Paraffins in Feed.

TABLE 1

| EXAMPLE | Olefins Conversion (%) | Paraffins Conversion (wt %) | Propylene wt % in product | Ethylene wt% in product | Endotherm (° C.) |
|---|---|---|---|---|---|
| 1 | 67.4 | 2.4 | 13.8 | 6.2 | 14 |
| 2 | 64 | 33.6 | 18.2 | 8.3 | 24 |

Example 2

Example 1 was repeated using a light coker naphtha as the feedstock, with the composition given in Table 2. All testing conditions were the same as in Example 1. As shown in Table 1, although the olefins conversion was comparable with the conversion in Example 1, 64 wt % vs. 67 wt %, the paraffins conversion was significantly higher, i.e., 33.6 wt % vs. 2.4 wt %. The C5-C6 longer chain paraffins present in the light coker naphtha (Table 2) are easier to crack over the cracking catalyst compared to a shorter chain paraffin (iso-butane).

Supporting the high paraffins conversion observed with the light coker naphtha feed with 44 wt % C4-C7 paraffins, is the very high reaction endotherm recorded during the test in Example 2, i.e., 24° C., vs. only 14° C. in Example 1 with a feed with 60% iso-butane, also included in Table 1. As mentioned, iso-butane, and in general shorter chain paraffins, are more difficult to crack.

TABLE 2

| Compositions | wt % |
|---|---|
| C4P | 2.010 |
| C4O | 1.391 |
| C4DO | 0.033 |
| C5P | 20.637 |
| C5O | 20.713 |
| C5DO | 1.122 |
| C5N | 1.357 |
| C6P | 20.798 |
| C6O | 24.183 |
| C6DO | 0.396 |
| C6N | 2.822 |
| C7P | 0.662 |
| C7O | 1.731 |
| C7DO | 0.364 |
| C7N | 0.055 |
| A6 | 0.428 |
| A7 | 0.015 |
| Heavier compds | 1.282 |

Where P = paraffins, O = olefins; N = naphthene; DO = di-olefins; A = aromatics

A number of embodiments of the invention have been described. Nevertheless, it can be understood that various modifications may be made without departing from the spirit and scope of the invention. Accordingly, other embodiments are within the scope of the following claims.

The term "column" means a distillation column or columns for separating one or more components of different volatilities. Each column may include a condenser on an overhead of the column to condense the overhead vapor and reflux a portion of an overhead stream back to the top of the column.

The term "stream" can include various hydrocarbon molecules and other substances.

The term "heavies" means heavy hydrocarbons, such as $C_{9+}$ hydrocarbons, and can also include unconverted oil comprising $C_{9+}$ hydrocarbons produced in a reactor or reaction chamber.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 75%, 80%, 85%, 90%, 91%, 92%, 93%, 94%, 95%, 96%, 97%, 98%, 99% or 99.5%, or more of a referenced amount of a composition.

This detailed description is merely exemplary in nature and is not intended to limit the various embodiments or the application and uses thereof. The figures have been simplified by the deletion of various devices or apparatuses customarily employed in an OCP process of this nature, including by not limited to vessel internals, temperature and pressure controls systems, connections to computers and the computers (or other memory devices) for controlling systems for carrying out methods as provided herein, flow control valves, recycle pumps, and the like, which are not specifically required to illustrate the performance of exemplary methods as provided herein. Illustrations of exemplary processes in drawings as provided herein are not intended to limit the invention to specific embodiments illustrated or described set out herein.

Any line, conduit, unit, device, vessel, surrounding environment, zone or the like used to practice processes as provided herein can be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof. In alternative embodiments, sensors are present on all lines or streams so that the corresponding parameter(s) can be monitored and/or controlled as desired or needed.

Signals, measurements, and/or data generated or recorded by monitoring components may be transmitted to one or more computing devices or systems. In alternative embodiments, processes as provided herein comprise use of computing devices or systems that may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

The details of one or more exemplary embodiments of the invention are set forth in the accompanying drawings and the description above. Other features, objects, and advantages of the invention will be apparent from the description and drawings, and from the claims.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

Specific Embodiments

While the following is described in conjunction with specific embodiments, it will be understood that this description is intended to illustrate and not limit the scope of the preceding description and the appended claims.

A first embodiment of the invention is a process comprising cracking a feed stream comprising $C_{4+}$ olefins and paraffins in an olefin cracking reactor of a cracking zone forming an olefin cracking reactor effluent stream, wherein the olefin reactor effluent stream comprises ethylene, propylene, $C_4$ to $C_{10}$ olefins, and 10 wt % or more of $C_4$ to $C_8$ paraffins separating the olefin reactor effluent stream into at least an olefin product stream comprising ethylene and propylene, a $C_4$-$C_5$ stream comprising butanes and pentanes; dividing the $C_4$-$C_5$ stream into a paraffin-rich recycle stream and a purge stream; cracking the paraffin-rich recycle stream in the paraffin cracking reactor of the cracking zone forming a paraffin reactor effluent stream comprising ethylene and propylene, $C_4$-$C_{10}$ olefins, and a reduced level of paraffins compared to the paraffin-rich recycle stream; and cracking the paraffin reactor effluent stream in the olefin cracking reactor; whereby the olefin reactor effluent stream comprises a level of ethylene and propylene greater than a level of ethylene and propylene in an olefin reactor effluent stream from an olefin cracking zone without a paraffin cracking reactor. An embodiment of the invention is one, any or all of prior embodiments in this paragraph up through the first embodiment in this paragraph further comprising heating the feed stream before cracking the feed stream; or heating the paraffin-rich recycle stream before cracking the paraffin-rich recycle stream in the paraffin cracking reactor; or both. An embodiment of the invention is one, any or all of prior embodiments in this paragraph up through the first embodiment in this paragraph wherein the feed stream or the paraffin-rich recycle stream, or both are heated in a charge heater or by heat exchanging with the olefin reactor effluent stream, or both. An embodiment of the invention is one, any or all of prior embodiments in this paragraph up through the first embodiment in this paragraph wherein the feed stream and the paraffin-rich recycle stream are heated in a single charge heater with separate tubes. An embodiment of the invention is one, any or all of prior embodiments in this paragraph up through the first embodiment in this paragraph further comprising combining the feed stream and the paraffin reactor effluent stream forming a combined stream; heating the combined stream before cracking the feed stream and the paraffin reactor effluent stream in the olefin cracking reactor, wherein cracking the feed stream and the paraffin reactor effluent stream comprises cracking the combined stream. An embodiment of the invention is one, any or all of prior embodiments in this paragraph up through the first embodiment in this paragraph further comprising compressing the olefin reactor effluent stream before separating the olefin reactor effluent stream. An embodiment of the invention is one, any or all of prior embodiments in this paragraph up through the first embodiment in this paragraph wherein the olefin cracking reactor and the paraffin cracking reactor are separate beds in a single reactor vessel. An embodiment of the invention is one, any or all of prior embodiments in this paragraph up through the first embodiment in this paragraph wherein the olefin cracking reactor and the paraffin cracking reactor are in separate vessels. An embodiment of the invention is one, any or all of prior embodiments in this paragraph up through the first embodiment in this paragraph wherein the feed stream and the paraffin reactor effluent stream are fed at different locations in a single reactor vessel. An embodiment of the invention is one, any or all of prior embodiments in this paragraph up through the first embodiment in this paragraph wherein the olefin cracking reactor and the paraffin cracking reactor contain the same catalyst. An embodiment of the invention is one, any or all of prior embodiments in this paragraph up through the first embodiment in this paragraph wherein the olefin cracking reactor and the paraffin cracking reactor contain different catalysts. An embodiment of the invention is one, any or all of prior embodiments in this paragraph up through the first embodiment in this paragraph wherein the olefin cracking reactor or the paraffin cracking reactor or both comprise a catalyst, and the catalyst comprises a silicalite having a silica to alumina ratio greater than 200, and wherein the silicalite is steam treated, acid washed, and loaded with an alkaline earth metal. An embodiment of the invention is one, any or all of prior embodiments in this paragraph up through the first embodiment in this paragraph wherein the olefin cracking reactor comprises a catalyst comprising a silicalite having a silica to alumina ratio greater than 200, and wherein the paraffin cracking reactor comprises a catalyst comprising an acidic catalyst. An embodiment of the invention is one, any or all of prior embodiments in this paragraph up through the first embodiment in this paragraph wherein an operating temperature of the olefin cracking reactor ranges from about 560° C. to about 620° C. An embodiment of the invention is one, any or all of prior embodiments in this paragraph up through the first embodiment in this paragraph wherein an operating temperature of the paraffin cracking reactor ranges from about 490° C. to about 620° C. An embodiment of the invention is one, any or all of prior embodiments in this paragraph up through the first embodiment in this paragraph further comprises selectively hydrogenating feed stream before feeding the paraffin-rich feed stream to the olefin cracking reactor.

A second embodiment of the invention is a process comprising cracking a feed stream comprising $C_{4+}$ olefins and paraffins in an olefin cracking reactor of a cracking zone forming an olefin cracking reactor effluent stream, wherein the olefin reactor effluent stream comprises ethylene, propylene, $C_4$ to $C_{10}$ olefins, and 10 wt % or more of $C_4$ to $C_8$ paraffins compressing the olefin reactor effluent stream; separating the compressed olefin reactor effluent stream into at least an olefin product stream comprising ethylene and propylene, a $C_4$-$C_5$ stream comprising butanes and pentanes, and a heavy stream comprising $C_{6+}$ hydrocarbons; dividing the $C_4$-$C_5$ stream into a paraffin-rich recycle stream and a purge stream; cracking the paraffin-rich recycle stream in the paraffin cracking reactor of the cracking zone forming a paraffin reactor effluent stream comprising ethylene and propylene, $C_4$-$C_{10}$ olefins, and a reduced level of paraffins compared to the paraffin-rich recycle stream; cracking the paraffin reactor effluent stream in the olefin cracking reactor; and heating the feed stream before cracking the feed stream, or heating the paraffin-rich recycle stream before cracking the paraffin-rich recycle stream in the paraffin cracking reactor, or both; whereby the olefin reactor effluent stream comprises a level of ethylene and propylene greater than a level of ethylene and propylene in an olefin reactor effluent stream from an olefin cracking zone without a paraffin cracking reactor. An embodiment of the invention is one, any or all of prior embodiments in this paragraph up through the second embodiment in this paragraph wherein the feed stream and the paraffin reactor effluent stream are fed at different locations in a single reactor vessel. An embodiment of the invention is one, any or all of prior embodiments in this paragraph up through the second embodiment in this paragraph wherein the olefin cracking reactor or the paraffin cracking reactor or both comprise a catalyst, and the catalyst comprises a silicalite having a silica to alumina ratio greater than 200, and wherein the silicalite is steam treated, acid washed, and loaded with an alkaline earth metal. An embodiment of the invention is one, any or all of prior embodiments in this paragraph up through the second embodiment in this paragraph wherein the olefin cracking reactor comprises a catalyst comprising a silicalite having a silica to alumina ratio greater than 200, and wherein the paraffin cracking reactor comprises a catalyst comprising an acidic catalyst.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process comprising:

cracking a feed stream comprising $C_{4+}$ olefins and paraffins in an olefin cracking reactor of a cracking zone forming an olefin cracking reactor effluent stream, wherein the olefin reactor effluent stream comprises ethylene, propylene, $C_4$ to $C_{10}$ olefins, and 10 wt % or more of $C_4$ to $C_8$ paraffins:

separating the olefin reactor effluent stream into at least an olefin product stream comprising ethylene and propylene, a $C_4$-$C_5$ stream comprising butanes and pentanes;

dividing the $C_4$-$C_5$ stream into a paraffin-rich recycle stream and a purge stream;

cracking the paraffin-rich recycle stream in a paraffin cracking reactor of the cracking zone forming a paraffin reactor effluent stream comprising ethylene and propylene, $C_4$-$C_{10}$ olefins, and a reduced level of paraffins compared to the paraffin-rich recycle stream; and cracking the paraffin reactor effluent stream in the olefin cracking reactor.

2. The process of claim 1 further comprising:

heating the feed stream before cracking the feed stream; or heating the paraffin-rich recycle stream before cracking the paraffin-rich recycle stream in the paraffin cracking reactor; or both.

3. The process of claim 2 wherein the feed stream or the paraffin-rich recycle stream, or both are heated in a charge heater or by heat exchanging with the olefin reactor effluent stream, or both.

4. The process of claim 3 wherein the feed stream and the paraffin-rich recycle stream are heated in a single charge heater with separate tubes.

5. The process of claim 1 further comprising:

combining the feed stream and the paraffin reactor effluent stream forming a combined stream; and heating the combined stream before cracking the combined stream in the olefin cracking reactor, wherein cracking the feed stream and the paraffin reactor effluent stream comprises cracking the combined stream.

6. The process of claim 1 further comprising:

compressing the olefin reactor effluent stream before separating the olefin reactor effluent stream.

7. The process of claim 1 wherein the olefin cracking reactor and the paraffin cracking reactor are separate beds in a single reactor vessel.

8. The process of claim 1 wherein the olefin cracking reactor and the paraffin cracking reactor are in separate vessels.

9. The process of claim 7 wherein the feed stream and the paraffin reactor effluent stream are fed at different locations in a single reactor vessel.

10. The process of claim 1 wherein the olefin cracking reactor and the paraffin cracking reactor contain the same catalyst.

11. The process of claim 1 wherein the olefin cracking reactor and the paraffin cracking reactor contain different catalysts.

12. The process of claim 1 wherein the olefin cracking reactor or the paraffin cracking reactor or both comprise a catalyst, and the catalyst comprises a silicalite having a silica to alumina ratio greater than 200, and wherein the silicalite is steam treated, acid washed, and loaded with an alkaline earth metal.

13. The process of claim 1 wherein the olefin cracking reactor comprises a catalyst comprising a silicalite having a silica to alumina ratio greater than 200, and wherein the paraffin cracking reactor comprises a catalyst comprising an acidic catalyst.

14. The process of claim 1 wherein an operating temperature of the olefin cracking reactor ranges from about 560° C. to about 620° C.

15. The process of claim 1 wherein an operating temperature of the paraffin cracking reactor ranges from about 490° C. to about 620° C.

16. The process of claim 1 further comprises:

selectively hydrogenating feed stream before feeding the paraffin-rich feed stream to the olefin cracking reactor.

17. A process comprising:

cracking a feed stream comprising $C_{4+}$ olefins and paraffins in an olefin cracking reactor of a cracking zone forming an olefin cracking reactor effluent stream, wherein the olefin reactor effluent stream comprises ethylene, propylene, $C_4$ to $C_{10}$ olefins, and 10 wt % or more of $C_4$ to $C_8$ paraffins:

compressing the olefin reactor effluent stream;

separating the compressed olefin reactor effluent stream into at least an olefin product stream comprising ethylene and propylene, a $C_4$-$C_5$ stream comprising butanes and pentanes, and a heavy stream comprising $C_{6+}$ hydrocarbons;

dividing the $C_4$-$C_5$ stream into a paraffin-rich recycle stream and a purge stream;

cracking the paraffin-rich recycle stream in a paraffin cracking reactor of the cracking zone forming a paraffin reactor effluent stream comprising ethylene and propylene, $C_4$-$C_{10}$ olefins, and a reduced level of paraffins compared to the paraffin-rich recycle stream;

cracking the paraffin reactor effluent stream in the olefin cracking reactor; and heating the feed stream before cracking the feed stream, or heating the paraffin-rich recycle stream before cracking the paraffin-rich recycle stream in the paraffin cracking reactor, or both.

18. The process of claim 17 wherein the feed stream and the paraffin reactor effluent stream are fed at different locations in a single reactor vessel.

19. The process of claim 17 wherein the olefin cracking reactor or the paraffin cracking reactor or both comprise a catalyst, and the catalyst comprises a silicalite having a silica to alumina ratio greater than 200, and wherein the silicalite is steam treated, acid washed, and loaded with an alkaline earth metal.

20. The process of claim 17 wherein the olefin cracking reactor comprises a catalyst comprising a silicalite having a silica to alumina ratio greater than 200, and wherein the paraffin cracking reactor comprises a catalyst comprising an acidic catalyst.

* * * * *